United States Patent

Hocker et al.

[11] B 3,985,789
[45] Oct. 12, 1976

[54] CARBAMIC ACID ESTERS

[75] Inventors: Jürgen Hocker, Schildgen; Hans-Joachim Diehr, Wuppertal; Rudolf Merten, Leverkusen, all of Germany

[73] Assignee: Bayer Aktiengesellschaft, Leverkusen, Germany

[22] Filed: May 22, 1974

[21] Appl. No.: 472,256

[44] Published under the second Trial Voluntary Protest Program on January 13, 1976 as document No. B 472,256.

[30] Foreign Application Priority Data

May 22, 1973 Germany............................ 2325927

[52] U.S. Cl. ......................... 260/472; 260/247.2 B; 260/248 NS; 260/293.74; 260/468 E; 260/479 C
[51] Int. Cl.²..................................... C07C 125/06
[58] Field of Search .................................... 260/472

[56] References Cited
UNITED STATES PATENTS 3,803,062   4/1974   Rodia et al. ...................... 260/472

*Primary Examiner*—Richard L. Raymond
*Attorney, Agent, or Firm*—Joseph C. Gil; Gene Harsh

[57] ABSTRACT

Novel compounds which upon heating are converted into the corresponding phenol which is a catalyst for the trimerization of compounds having isocyanato groups to form isocyanurates have the formula:

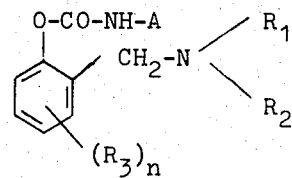

in which
$n$ represents an integer of from 1 to 4
A represents an aromatic hydrocarbon group obtained by removing the NCO group from a monomeric aromatic monoisocyanate containing 6 – 14 carbon atoms,
$R_1$ and $R_2$ may be the same or different and represent a $C_1$ to $C_6$ alkyl group or a polymethylene chain containing 4 to 8 carbon atoms which together with a nitrogen atom form a heterocyclic ring,
$R_3$ may be hydrogen, chlorine, bromine or a $C_1$ – $C_{18}$-alkyl group.

2 Claims, No Drawings

CARBAMIC ACID ESTERS

This invention relates generally to carbamic acid esters and more particularly to novel carbamic acid esters which are catalysts for the trimerization of isocyanato groups containing compounds and to a method for making them.

Mannich bases which have an ortho phenolic OH group prepared by reaction of phenols, aldehydes and secondary amines are known catalysts for converting isocyanates into the corresponding isocyanurates (Kunststoff Volume 62, page 731 (1972)).

The catalytic activity of these compounds is believed to be due to the simultaneous presence of the free phenolic hydroxyl group and the aminoalkyl group in the ortho-position to this phenolic hydroxyl group. This means that the corresponding compounds in which the phenolic hydroxyl groups are masked do not manifest this catalytic activity. Suitable Mannich bases which have masked phenolic hydroxyl groups which can be converted into the corresponding phenols when heated should, therefore, be valuable isocyanate trimerization catalysts which would be inactive at room temperature but could be activated by heat.

Phenols can be converted in known manner by reaction with isocyanates into N-substituted carbamic acid phenyl esters which will dissociate again when heated, but it was not expected that this principle would be applicable to the aforesaid Mannich bases with phenolic hydroxyl groups. This is so because one would expect the competing reaction to predominate, namely the trimerization reaction which is catalyzed by Mannich bases.

It is therefore an object of this invention to provide novel N-substituted carbamic acid phenyl esters. Another object of the invention is to provide a method for making the novel N-substituted carbamic acid phenyl esters. A more specific object of the invention is to provide Mannich bases having masked phenolic hydroxyl groups which dissociate upon heating into the corresponding phenol and becomes catalysts for the trimerization of isocyanates. It is a still further object of the present invention to provide a process for trimerizing a compound having isocyanato groups to form an isocyanurate which comprises heating a compound having isocyanato groups and a catalytic amount of a Mannich base having masked phenolic hydroxyl groups as hereinafter described.

The foregoing objects and others are accomplished in accordance with this invention, generally speaking, by providing compounds of the general formula

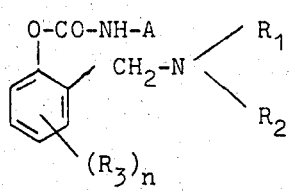

in which
n represents an integer of from 1 to 4
A represents an aromatic hydrocarbon group obtained by removing the NCO group from a monomeric aromatic monoisocyanate containing 6 – 14 carbon atoms,
$R_1$ and $R_2$ may be the same or different and represent a $C_1$ to $C_6$ alkyl group or a polymethylene chain containing 4 to 8 carbon atoms which together with a nitrogen atom form a heterocyclic ring,
$R_3$ may be hydrogen, chlorine, bromine or a $C_1$ - $C_{18}$ - alkyl group.

It has now surprisingly been found that new N-substituted (2-dialkylaminomethyl)-phenylesters of carbamic acid of the above formula can be obtained from the corresponding phenols and aromatic isocyanates if certain reaction conditions are observed. These new phenyl carbamates are valuable catalysts for the trimerization of organic isocyanates which can be activated by heat.

This invention also provides a process for preparing organic compounds of the general formula

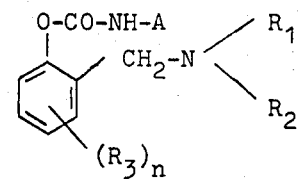

which is characterized in that phenols of the general formula

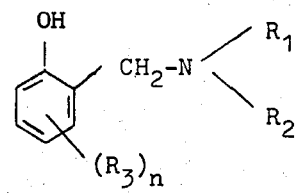

are reacted at −20° to +60°C with isocyanates of the general formula
 A NCO
in which n, $R_1$, $R_2$, $R_3$ and A have the meaning hereinbefore set forth.

Mannich bases of the general formula

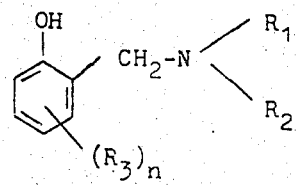

which are suitable for use in the process according to the invention may be obtained in known manner from the corresponding phenols of the general formula

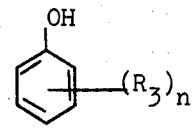

formaldehyde and the corresponding amines

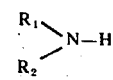

by a conventional Mannich reaction. In these formulae, the groups R₁ – R₃ and n have the meanings indicated above.

Such Mannich reactions between phenols, aldehydes and secondary amines have already been described, for example, in "α-Aminoalkylierung" by H. Hellmann and G. Opitz, publishers Verlag Chemie 1960.

The following are examples of Mannich bases which are suitable for use in the process according to the invention:

2-(Dimethylaminomethyl)-phenol,
2-(di-n-butylaminomethyl)-phenol,
2-(piperidinomethyl)-phenol,
2-(dimethylaminomethyl)- 4,6-dimethylphenol,
2-di-n-butylaminomethyl)-4,6-dimethylphenol,
2-(piperidinomethyl)-4,6-dimethylphenol,
2-(dimethylaminomethyl)-4-isononylphenol),
2-(di-n-butylaminomethyl)-4-isononylphenol,
2-(piperidinomethyl)-4-isononylphenol,
2-(morpholinomethyl)-4,6-dimethylphenol,
2-(dimethylaminomethyl)-4,6-di-tert.-butylphenol, and
2-(dimethylaminomethyl)-3,4,6-trichlorophenol.

Any monoisocyanate which contains an aromatically bound isocyanato group of the general formula

A—NCO is suitable for reaction with the Mannich base in accordance with the invention such as, for example, phenylisocyanate, p-methyl-phenylisocyanate, p-methyl-naphthyl-isocyanate, and the like, and the corresponding nitro substituted, halogenated or alkoxy substituted isocyanates such as p-nitrophenylisocyanate, p-chlorophenyl-isocyanate, p-methoxyphenylisocyanate and the like.

The process according to the invention is carried out at temperatures between about −20°C and about 60°C, preferably between about 0°C and about 40°C. The isocyanate is preferably added in the equivalent quantity (NCO/OH ratio = 1:1) to the Mannich base. The reaction may be carried out either solvent-free or in the presence of a suitable inert solvent for the reactants such as petroleum ether, cyclohexane, benzene, toluene, xylene, methylene chloride, chloroform, carbon tetrachloride, chlorobenzene, dichlorobenzene, acetone, methyl ethyl ketone, acetonitrile, dimethylformamide or ethyl acetate. Termination of the reaction can be detected by the disappearance of free isocyanato groups, for example in the IR spectrum.

The reaction mixture is worked up by the usual methods of preparative organic chemistry. Temperatures above 60°C should be as far as possible avoided because the new products of the process begin to dissociate into their starting components at temperature above 70°C. For this reason, the new products of the process are valuable catalysts which can be activated by heat for isocyanate chemistry, in particular for the trimerization of isocyanate.

The compounds provided by this invention as well as compounds of the general formula

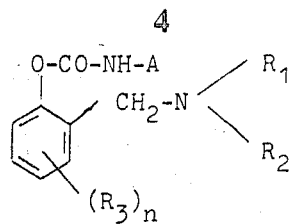

in which
n, R₁, R₂ and R₃ have the meanings already indicated hereinbefore and A stands for an aliphatic hydrocarbon radical having 1 to 18 carbon atoms or a cyclo-aliphatic hydrocarbon radical having from 5 to 10 carbon atoms which latter compounds per se are not an object of the present invention can be used in catalytic amounts for catalyzing the polymerization of isocyanates to form isocyanurates. The isocyanurate may be produced by mixing an isocyanato terminated compound with the catalyst in an amount of from 5 to 50 preferably 10 to 30 parts by weight of catalysts per 100 parts by weight of the isocyanato terminated compound and heating the mixture to above the dissociation temperature of the catalyst into one having a free phenolic hydroxyl group, e.g. to 70° to 200°C according to the procedures which are disclosed in U.S. Pat. No. 3,580,868. The isocyanurates produced using the catalyst of the invention are useful for example, for the production of lacquers which may be formed with solvents and applied to all sorts of different substrates such as wood, glass, metal, paper or the like.

The invention is further illustrated by the following working examples.

EXAMPLE 1

N-Phenylcarbamic acid-2-(piperidinomethyl)-4,6-dimethylphenyl-ester 29.75 g (0.25 mol) of phenylisocyanate are introduced dropwise at 0° to 5°C into a solution of 54.75g (0.25 mol) of 2-(piperidinomethyl)-4,6-dimethylphenol in 80 ml of anhydrous benzene. The reaction mixture is stirred at room temperature for 4 hours. The precipitated carbamic acid ester is suction filtered and washed with petroleum ether (b.p. 30°–50°C).

Yield: 50.5g, m.p. 120°–122°C (with decomposition).

EXAMPLE 2

59.5 g (0.5 mol) of phenylisocyanate are introduced dropwise into a solution of 138.5 g (0.5 mol) of a crude 2-(dimethylaminomethyl)-4-isononylphenol in 100 ml of petroleum ether (b.p. 30°–50°C) at 0° to 5°C. The reaction mixture is then stirred for one hour at room temperature and the solvent is distilled off under vacuum at a bath temperature of 30°C. 192 g of a viscous oil which has the characteristic carbonyl band for urethanes at 1690 to 1710⁻¹ in the IR spectrum are obtained.

EXAMPLE 3

125 parts by weight of phenylisocyanate are added dropwise with vigorous stirring to 361 parts by weight of 2-(di-n-butylaminomethyl)-4-isononylphenol (isomeric mixture) in the course of 3½ hours at 0° to 20°C. A very viscous liquid which crystallizes only with difficulty is obtained. It shows the characteristic carbonyl absorption at 1715 cm⁻¹ in the IR spectrum

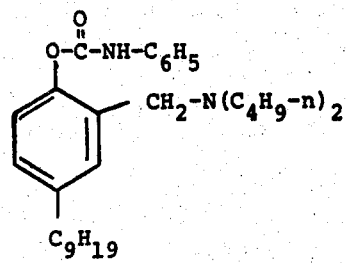

EXAMPLE 4

A solution of 8.5 g of 1-naphthylisocyanate (5 mmol) in 40 ml of toluene is added to 13.2 of 2-(dimethylaminomethyl)-4,6-di-tert.-butylphenol (5 mmol) at 20° to 30°C. The reaction mixture is then stirred for 6 hours at room temperature and suction filtered to isolate 14.9 g of the urethane. Colorless crystals melting at 122° to 136°C (decomposition) are obtained which have the characteristics carbonyl absorption for urethanes at 1740 cm$^{-1}$ in the IR spectrum.

Mass spectrum: m/e = 432.

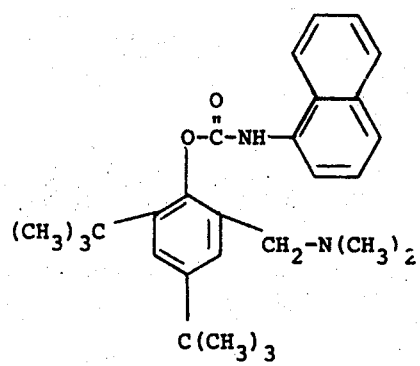

EXAMPLE 5

5.08 g (2 mmol) of 2-(dimethylaminomethyl)-3,4,6-trichlorophenol are dissolved in 10 ml of toluene, and a solution of 2.66 g (2 mmol) of m-tolylisocyanate in 10 ml of toluene is slowly added at 25°–30°C. The reaction mixture is then stirred at room temperature for 5 hours and then at 40°C for 5 hours. Addition of ether yields 3.4 g of the urethane with the characteristic carbonyl absorption in the IR spectrum at 1753 cm$^{-1}$.

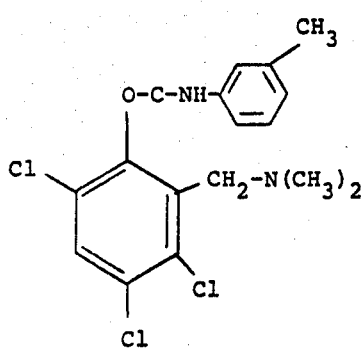

EXAMPLE 6

24 parts by weight of the compound of example 3, 4 parts by weight of a polysiloxane - polyether - copolymerizate as stabilizer (L 5320 of Union Carbide Corporation), 20 parts by weight of azo-isobutyric acid dinitrile as driving agent and 100 parts by weight of 4,4'-diisocyanatodiphenyl-methane are mixed at room temperature. Upon heating of the mixture for 30 minutes to 150°C an isocyanurate foam is obtained. Prior to this heating step the reaction mixture was storage stable for 12 hours at 10°C.

EXAMPLE 7

28.0 parts by weight of methylisocyanate are added within 6 hours to 53.7 parts by weight of 2-dimethylaminomethyl-4,6-dimethylphenol cooled to 0°C dropwise under stirring so that the reaction temperature does not rise above 15°C. The reaction product thus obtained does not show any catalytic activity on phenylisocyanate at room temperature.

The crystalline raw material which was formed in the course of the reaction is separated from excess liquid starting materials by filtration. Last traces of liquid raw materials are removed with white spirit.

36 parts by weight of a crystalline product having the formula

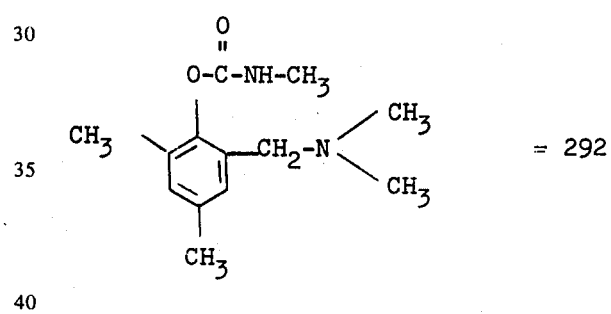

are obtained.

Analysis: Calculated: C, 66.1 %; H, 8.5%; N, 11.96%; Found: C, 65.7 %; H, 8.4%; N, 12.0%.

16 parts by weight of above catalysts,
3 parts by weight of the stabilizer of Example 6,
20 parts by weight of the driving agent of Example 6,
100 parts by weight of the diisocyanate of Example 6
are mixed at room temperature. This mixture is storage stable during a period of time of 48 hours at 20°C. Upon heating to 150°C for 30 minutes an isocyanurate foam is obtained.

EXAMPLE 8

59 parts by weight of methylisocyanate are added under stirring to 361 parts by weight of 2-(Di-n-butylaminomethyl)-4-isononylphenol during a period of time of 90 minutes at −5° to +5°C. A highly viscose liquid is obtained the IR-spectrum of which reveals the characteristic edge for urethane groups at 1720 cm$^{-1}$. The composition of matter obtained has practically no catalytic influence on polyisocyanate at room temperature.

If 17 parts by weight of this compound, 5 parts by weight of the stabilizer of Example 6, 20 parts by weight of the driving agent of Example 6 and 100 parts by weight of the diisocyanate of Example 6 are heated to 150°C for 30 minutes an isocyanurate foam is obtained.

EXAMPLE 9

32.2 parts by weight of stearylisocyanate are added under stirring to 27.7 parts by weight of 2-dimethylaminomethyl-4-isononylphenol at +5° to +15°C during a period of time of 3,5 hours. A highly viscous oil is obtained. The IR-spectrum of which having the characteristic edge for urethane groups at 1750cm$^{-1}$. A mixture of this compound with phenylisocyanate reveals to be storage stable during a period of time of 48 hours at 20°C.

If 32 parts by weight of this compound, 1 part by weight of the stabilizer of example 6, 15 parts by weight of the driving agent of Example 6, and 100 parts by weight of the diisocyanate of example 6 are heated to 150°C for 30 minutes an isocyanurate foam is obtained.

EXAMPLE 10

170 parts by weight of methylisocyanate are added dropwise under stirring within 11 hours at 0° to +15°C to 554 g of 2-(dimethylaminomethyl)-4-isononylphenol. A highly viscous liquid is obtained the IR-spectrum of which reveals the characteristic edge at 1715cm$^{-1}$ for urethane bonds.

If 21 parts by weight of this compound, 4 parts by weight of the stabilizer of Example 6, 20 parts by weight of the driving agent of Example 6, and 100 parts by weight of the diisocyanate of Example 6 are heated for 30 minutes to 150°C a isocyanurate foam is obtained.

Any of the other organic isocyanates and organic diisocyanates disclosed as suitable herein can be reacted with any of the Mannich bases disclosed as suitable herein to produce the corresponding masked Mannich base in accordance with the process described in the foregoing working examples.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A compound of the general formula

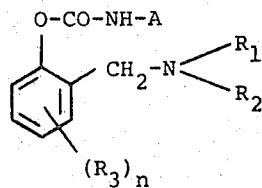

wherein $n$ represents an integer of from 1 to 4,

A represents an aromatic hydrocarbon group obtained by removing the NCO group from a monomeric aromatic monoisocyanate containing 6–14 carbon atoms, $R_1$ and $R_2$ may be the same or different and each represent a $C_1$-$C_6$ alkyl group, and $R_3$ represents hydrogen, chlorine, bromine, or a $C_1$-$C_{18}$ alkyl group.

2. A compound according to claim 1 wherein $R_1$ and $R_2$ each represent a methyl group.

* * * * *